United States Patent [19]
Goldstein

[11] Patent Number: 5,695,929
[45] Date of Patent: Dec. 9, 1997

[54] SUBSTITUTE SALIVA STANDARD

[76] Inventor: Andrew S. Goldstein, 7260 SW. Ascot, Portland, Oreg. 97225

[21] Appl. No.: 480,790

[22] Filed: Jun. 7, 1995

[51] Int. Cl.$^6$ .............................. C12Q 1/70; A61K 7/28; A61K 38/47; A01N 59/10
[52] U.S. Cl. .............. 435/5; 424/50; 424/94.61; 424/680; 514/780
[58] Field of Search ................ 435/5; 424/94.61, 424/50, 680; 514/780

[56] References Cited

U.S. PATENT DOCUMENTS

| | | | |
|---|---|---|---|
| 5,103,836 | 4/1992 | Goldstein et al. | 128/760 |
| 5,335,673 | 8/1994 | Goldstein et al. | 128/760 |
| 5,339,829 | 8/1994 | Thieme et al. | 128/760 |
| 5,494,665 | 2/1996 | Saito et al. | 424/94.61 |

FOREIGN PATENT DOCUMENTS

| | | | |
|---|---|---|---|
| WOA94 04078 | 3/1994 | WIPO | A61B 10/00 |
| WOA95 27205 | 3/1994 | WIPO | G01N 33/52 |

OTHER PUBLICATIONS

Int. J. Biochem. (1993), 25(5), 681–7 Coden: IJBOB-V;ISSN: 0020–711X, XP002015116 Slomiany, B.L. et al.: "Control of mucin molecular forms expression by salivary protease: differences with caries".

Physicians' Desk Reference, pp. 1211, 1378–1379.

Journal of Oral Pathology, 1983, 12:336–341 "Remineralization of Softened Human Enamel In Mucin–or CMC–Containing Artificial Salivas", T.B.F.M. Gelhard et al.

Human Saliva: Clinical Chemistry and Microbiology, vol. 1, Jorma O. Tenovuo et al., pp. 77–95.

Clinical and Diagnostic Virology 2(1994)231–243, "Detection of Antibody to HIV in Saliva: A Brief Review", Philip P. Mortimer et al.

*Primary Examiner*—Lynette F. Smith
*Assistant Examiner*—Brett L. Nelson
*Attorney, Agent, or Firm*—Townsend and Townsend and Crew LLP

[57] ABSTRACT

A substitute saliva standard for use in testing, calibration, and standardization of devices and methods for collecting and analyzing oral fluids.

12 Claims, No Drawings

SUBSTITUTE SALIVA STANDARD

BACKGROUND OF THE INVENTION

This invention relates to analysis of oral fluids and, more particularly, this invention relates to a standard to be used for testing, calibration, and standardization of devices and methods for collecting and analyzing oral fluids. This invention is not concerned with artificial salivas used for clinical purposes.

Analytical methods have been developed for determining the presence and/or amount of various substances in body fluids. Typically, in the past, blood or plasma was tested for antibodies or foreign substances such as alcohol or drugs. One goal has always been to be able to test body fluids which are non-invasively collected. To this end, for certain tests, urine is collected and tested. But, not all analytes show up in urine. Saliva would be the fluid of choice, but the concentration of the analytes in saliva is frequently lower than in the plasma.

Human saliva has been extensively studied and its composition is well-known (see, Jorma O. Tenovuo, ed., *Human Saliva: Clinical Chemistry and Microbiology*, Vol. I, pp. 77–95 (CRC Press, Inc. 1989). Various synthetic salivas have been developed for clinical therapeutic use. For instance, the product sold as GLANDOSANE® by Tsumura Medical is an aqueous solution of salts typically found in human saliva for use by patients suffering from hyposalivation or xerostomia, whether the condition is temporary or permanent. Another product is sold by MGI Pharma, Inc., as SALAGEN®. Additionally, studies have been made to improve some characteristics of the synthetic saliva products (see, T.B.F.M. Gelhard et al., "Remineralization of softened human enamel in mucin- or CMC-containing artificial salivas," *Journal of Oral Pathology* 1983: 12:336–341).

But, it is well-known that saliva is not uniform in composition. Various factors affect the actual makeup of saliva in individuals. The composition of saliva could vary depending, inter alia, on whether it is stimulated or unstimulated; from where in the oral cavity the sample is taken; time of day; and, transiently, diet (see, Tenovuo et al.).

Nowadays, analytical methods have been developed which are more sensitive. Also methods for collecting saliva have become more sophisticated. Andrew S. Goldstein et al. discovered that the concentration of antibodies and certain foreign substances is more concentrated in sub-mucosal transudate than in saliva per se, and developed methods and kits for collecting the sub-mucosal transudate (see, U.S. Pat. Nos. 5,103,836, 5,335,673, and 5,339,829). Others are developing methods and apparatuses for collecting oral samples, whether saliva per se or other secretions (see, Philip P. Mortimer et al., "Detection of antibody to HIV in saliva: a brief review," *Clinical and Diagnostic Virology*, Vol. 2, pp. 231–243 Elsevier Science B. V. 1994). But, there is not yet a standard against which these various collection devices are to be measured, nor is there a standard which can be used to compare different analytical methods. Furthermore, it is impractical to collect oral fluid in sufficient volume for use as a standardized reagent. There is, thus, a need for such an artificial saliva standard.

SUMMARY OF THE INVENTION

It is, therefore, a primary object of the present invention to provide a substitute saliva standard for use in testing, calibration, and standardization of devices and methods for collecting and analyzing oral fluids.

For ease of description, and without undue limitation, "saliva" will hereafter refer to oral fluid, regardless of where in the oral cavity it is secreted or how it is collected.

It is not the purpose of this invention to replicate saliva for clinical purposes. The composition of this invention is to be used as the standard for measuring the efficacy of saliva collection kits and for comparing and standardizing analytical methods. Consequently, the composition of this invention need not have precisely the same constituents in precisely the same proportions as those which would be required for a synthetic saliva for therapeutic use.

Generally, the inventive substitute saliva standard has the composition

| Ingredients | mmol/liter |
| --- | --- |
| Nitrite | 0.1–0.2 |
| Magnesium | 0.15–0.6 |
| Calcium | 0.5–0.47 |
| Sodium | 2–80 |
| Phosphate | 1.5–25 |
| Chloride | 10–56 |
| Potassium | 13–40 |
| Bicarbonate | 2–35 |
| Thimerosal | 0.01–0.1 g/100 ml |
| Amylase | 0.025–0.1 g/100 ml |
| Mucin (5%) | 0.02–0.5 g/liter |
| Antipain | 0.05 mg/liter |
| Deionized Water | QS to 1L (≈ 998 ml) |

In order to test a particular assay, a given amount of the substitute saliva standard is spiked with a predetermined amount of analyte, and the desired dilution made. The assay is then run. The substitute saliva standard could be spiked with, e.g., HIV antibody-positive serum, HIV antibody-negative serum, or any other target analyte which would ordinarily be detectable in human saliva. Representative of such analytes are those mentioned in the aforementioned U.S. Pat. No. 5,103,836, which is incorporated herein in its entirety by reference.

DETAILED DESCRIPTION OF THE PREFERRED EMBODIMENTS

The substitute saliva standard of the invention is first made up. A predetermined amount of the substitute saliva standard is spiked with whatever substance is to be detected.

EXAMPLE 1

Preparation of Substitute Saliva Standard Base

To make the substitute saliva standard of this invention, a 5% Mucin solution was first prepared by add 200 ml. of deionized water to 10 g. of Mucin and stirred until all the mucin was dissolved. Then the following ingredients were mixed in the order listed in about 800 ml of deionized water while stirring.

| Ingredients | mM/L | FW | g/L |
| --- | --- | --- | --- |
| $NaNO_2$ | 0.18 | 69.0 | 0.01 |
| $MgCl_2$ | 0.30 | 95.22 | 0.03 |
| $CaCl_2.2H_2O$ | 1.40 | 147.02 | 0.21 |
| NaCl | 10.5 | 58.44 | 0.61 |
| $KH_2PO_4$ | 12.0 | 136.09 | 1.63 |
| $K_2HPO_4$ | 2.90 | 174.2 | 0.50 |
| KCl | 13.4 | 74.55 | 1.00 |
| $NaHCO_3$ | 3.00 | 84.01 | 0.25 |
| Thimerosol | 0.02% | 404.8 | 0.20 |
| Amylase | | | 0.725 |
| Mucin (5%) | | | 2.0 ml |
| Antipain | 50 µg/ml | 604.7 | 0.05 |

After all the ingredients were dissolved, deionized water was added to make 1 liter and mixed thoroughly. The total amount of water to make 1 liter is about 998 ml. All the mixing may be at room temperature. It will be appreciated that it is not necessary to prepare 1 liter at a time. A batch may be made which is enough for immediate use, or a large amount may be made and frozen in aliquots of a predetermined size.

After the solution was made, a 25 ml. sample was removed and pH and conductivity measured. The pH should typically be 6.5±0.2. However, the pH can range from about 5.8 to about 7.8.

The solution was filtered once through 0.45 μm commercially available microporous filters and then passed through 0.2 μm microporous filters. Due to the viscous nature of the solution, filters became clogged so it was necessary to change filters often. A total of 10 filters were used in the first filtration step and two filters in the second. The solution should be stored at 4° C. until used.

EXAMPLE 2

Evaluation of HIV-1 Positive and HIV-1 Negative Serum

HIV-1 negative serum is titrated into substitute saliva standard base and tested in IgG EIA to determine the level of dilution necessary to obtain the target IgG level of 8–12 μg/ml. The HIV-1 positive serum is titrated into substitute saliva standard base as tested using the VIRONOSTIKA® HIV-1 Microelisa System made by Organon Teknika. The suggested starting point is a 1:200 dilution for a titration series of 11 dilutions. The proper total dilution is chosen taking into account the dilution when the substitute saliva standard is ultimately added to any preservative in the collection device used. For instance when using the ORASURE® collection system of Epitope, Inc., the dilution with preservative solution would be 1:3.

Using the negative serum dilution which is determined and the proper positive serum total dilution, the pre-dilution of the positive serum is calculated,

EXAMPLE 3

Formulation of Substitute Saliva Standard HIV-1 Positive

The following calculations are first completed:
1. Total volume of serum to spike $$1/y \times PBV = TV$$

where $1/y$ is predetermined dilution;
PBV is the planned batch volume (ml); and
TV is the total volume of serum to spike (ml).
2. Pre-dilution of high positive serum $$1/y \times TV = HP$$

where $1/y$ is as defined above;
TV is as defined above; and
HP is the volume of high positive serum.
3. Negative serum $$TV - HP = NS$$

where TV is as defined above;
Hp is as defined above; and

NS is the volume of negative serum.

The planned batch volume of substitute saliva standard base is measured and placed in a sterile container. A volume of substitute saliva standard base equal to TV is removed from the sterile container. The volume of high positive serum (HP) calculated above is added, the volume of negative serum (NS) calculated above is added and then mixed thoroughly. The solution is stored at 4° C. until needed.

EXAMPLE 4

Formulation of Substitute Saliva Standard HIV-1 Negative

The following calculations are first completed:
1. Total volume of serum to spike $$1/y \times PBV = TVNS$$

where $1/y$ is predetermined dilution;
PBV is the planned batch volume (ml); and
TVNS is the total volume of negative serum to spike (ml).

The planned batch volume of substitute saliva standard base is measured and placed in a sterile container. A volume of substitute saliva standard base equal to TVNS is removed from the sterile container. The volume of negative serum (TVNS) calculated above is added and then mixed thoroughly. The solution may be stored at 4° C. until needed.

EXAMPLE 5

Simulated Collection

A desired number of collection device packages are opened and treated with the substitute saliva standard positive or negative solution. In the case of Epitope, Inc.'s ORASURE® collection devices which use absorbent collection pads, the collection pads are placed onto plastic wrap. 400 μl of the substitute saliva standard reagent is carefully pipetted onto each pad. The pads are covered by folding the plastic wrap over them to prevent evaporation and held at room temperature for 5 to 30 minutes. The pads are then placed in their respective specimen vials, the handles are snapped off, the vials are capped, and then the vials are incubated at room temperature for at least one hour. The samples are then eluted as described in the aforementioned U.S. Pat. No. 5,103,836. Following elution, the samples are tested using any known HIV-1 ELISA test.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Substitute saliva standard for use in analysis of oral fluids comprising an aqueous solution of:

| | |
|---|---|
| Nitrite | 0.1–0.2 mmol/liter; |
| Magnesium | 0.15–0.6 mmol/liter; |
| Calcium | 0.5–0.47 mmol/liter; |
| Sodium | 2–80 mmol/liter; |
| Phosphate | 1.5–25 mmol/liter; |
| Chloride | 10–56 mmol/liter; |
| Potassium | 13–40 mmol/liter; |

| | |
|---|---|
| Bicarbonate | 2-35 mmol/liter; |
| Thimerosal | 0.01-0.1 g/100 ml; |
| Amylase | 0.025-0.1 g/100 ml; |
| Mucin (5%) | 0.02-0.5 g/liter; |
| Antipain | 0.05 mg/liter; and |
| Water | QS to 1L (≈998 ml). |

2. A substitute saliva standard as claimed in claim 1, wherein said water is deionized water.

3. A substitute saliva standard as claimed in claim 1, further including IgG-positive human serum.

4. A substitute saliva standard as claimed in claim 1, further including IgG-negative human serum.

5. A substitute saliva standard as claimed in claim 1, further including HIV antibody-positive human serum.

6. A substitute saliva standard as claimed in claim 5, wherein said HIV is HIV-1.

7. A substitute saliva standard as claimed in claim 1, further including HIV antibody-negative human serum.

8. A substitute saliva standard as claimed in claim 7, wherein said HIV is HIV-1.

9. A substitute saliva standard as claimed in claim 1, comprising an aqueous solution of:

| | |
|---|---|
| $NaNO_2$ | 0.01 g/L; |
| $MgCl_2$ | 0.03 g/L; |
| $CaCl_2.2H_2O$ | 0.21 g/L; |
| NaCl | 0.61 g/L; |
| $KH_2PO_4$ | 1.63 g/L; |
| $K_2HPO_4$ | 0.50 g/L; |
| KCl | 1.00 g/L; |
| $NaHCO_3$ | 0.25 g/L; |
| Thimerosol | 0.20 g/L; |
| Amylase | 0.725 g/L; |
| Mucin (5%) | 2.0 ml; and |
| Antipain | 0.05 g/L. |

10. A method of preparing an antibody-positive reagent for evaluating an assay to be used for assaying saliva, comprising:

(A) obtaining a predetermined batch volume of a substitute saliva standard comprising an aqueous solution of:

| | |
|---|---|
| Nitrite | 0.1-0.2 mmol/liter; |
| Magnesium | 0.15-0.6 mmol/liter; |
| Calcium | 0.5-0.47 mmol/liter; |
| Sodium | 2-80 mmol/liter; |
| Phosphate | 1.5-25 mmol/liter; |
| Chloride | 10-56 mmol/liter; |
| Potassium | 13-40 mmol/liter; |
| Bicarbonate | 2-35 mmol/liter; |
| Thimerosal | 0.01-0.1 g/100 ml; |
| Amylase | 0.025-0.1 g/100 ml; |
| Mucin (5%) | 0.02-0.5 g/liter; |
| Antipain | 0.05 mg/liter; and |
| Deionized Water | QS to 1L (≈ 998 ml); |

(B) selecting a positive serum that contains a desired antibody and a negative serum in which said desired antibody is absent;

(C) determining the total volume of serum to be used according to the relationship $$1/y \times PBV = TV$$

where 1/y is a predetermined dilution,
PBV is the planned batch volume (ml), and
TV is the total volume of serum to be used (ml);

(D) determining the amount of positive serum to be used according to the relationship $$1/y \times TV = HP,$$

where 1/y is as defined above,
TV is as defined above, and
HP is the volume of positive serum;

(E) determining the amount of negative serum to be used according to the relationship $$TV - HP = NS$$

where TV is as defined above,
HP is as defined above, and
NS is the volume of negative serum; and (F) combining the volumes of positive serum and negative serum as determined in steps (D) and (E) to an amount of the substitute saliva standard equal to the total volume of serum determined in step (C).

11. A method as claimed in claim 10, wherein said substitute saliva standard comprises an aqueous solution of:

| | |
|---|---|
| $NaNO_2$ | 0.01 g/L; |
| $MgCl_2$ | 0.03 g/L; |
| $CaCl_2.2H_2O$ | 0.21 g/L; |
| NaCl | 0.61 g/L; |
| $KH_2PO_4$ | 1.63 g/L; |
| $K_2HPO_4$ | 0.50 g/L; |
| KCl | 1.00 g/L; |
| $NaHCO_3$ | 0.25 g/L; |
| Thimerosol | 0.20 g/L; |
| Amylase | 0.725 g/L; |
| Mucin (5%) | 2.0 ml; and |
| Antipain | 0.05 g/L. |

12. A method of preparing an antibody-negative reagent for evaluating an assay to be used for assaying saliva, comprising:

(A) obtaining a predetermined batch volume of a substitute saliva standard comprising an aqueous solution of:

| | |
|---|---|
| Nitrite | 0.1-0.2 g/L; |
| Magnesium | 0.15-0.6 g/L; |
| Calcium | 0.5-0.47 g/L; |
| Sodium | 2-80 g/L; |
| Phosphate | 1.5-25 g/L; |
| Chloride | 10-56 g/L; |
| Potassium | 13-40 g/L; |
| Bicarbonate | 2-35 g/L; |
| Thimerosal | 0.01-0.1 g/100 ml; |
| Amylase | 0.025-0.1 g/100 ml; |
| Mucin (5%) | 0.02-0.5 g/liter; |
| Antipain | 0.05 mg/liter; and |
| Deionized Water | QS to 1L (≈ 998 ml); |

(B) selecting serum which is negative to desired antibodies;

(C) determining the total volume of serum to be used according to the relationship $$1/y \times PBV = TVNS$$

where 1/y is a predetermined dilution, PBV is the planned batch volume (ml), and TVNS is the total volume of negative serum to be used (ml); and (D) adding the volume of negative serum as determined in step (C) to an equal amount of the substitute saliva standard.

* * * * *